(12) United States Patent
Franco

(10) Patent No.: US 6,607,525 B2
(45) Date of Patent: Aug. 19, 2003

(54) APPARATUS AND METHOD FOR TREATING URINARY STRESS INCONTINENCE

(76) Inventor: Nicolas Franco, 5448 Dayna Ct., New Orleans, LA (US) 70124

( * ) Notice: Subject to any disclaimer, the term of this patent is extended or adjusted under 35 U.S.C. 154(b) by 0 days.

(21) Appl. No.: 09/920,560

(22) Filed: Aug. 1, 2001

(65) Prior Publication Data

US 2003/0028180 A1 Feb. 6, 2003

(51) Int. Cl.$^7$ .............................................. A61B 18/18
(52) U.S. Cl. ............................. 606/14; 606/12; 606/15; 606/119; 606/193; 607/40; 607/41; 607/89; 604/20; 604/21; 604/915
(58) Field of Search ............................. 606/2.5, 10–16, 606/20–23, 27, 28, 108, 119, 191–193; 607/40, 41, 88, 89, 92; 604/20, 21, 915, 920

(56) References Cited

U.S. PATENT DOCUMENTS

| | | | |
|---|---|---|---|
| 4,248,214 A | | 2/1981 | Hannah et al. |
| 5,032,124 A | | 7/1991 | Menton |
| 5,342,353 A | | 8/1994 | Allen |
| 5,454,807 A | | 10/1995 | Lennox et al. |
| 5,800,378 A | * | 9/1998 | Edwards et al. ............... 604/22 |
| 6,091,995 A | * | 7/2000 | Ingle et al. .................. 607/138 |
| 6,096,030 A | | 8/2000 | Ortiz |
| 6,123,083 A | | 9/2000 | McGrath et al. |
| 6,156,032 A | * | 12/2000 | Lennox ........................ 606/41 |
| 6,292,700 B1 | | 9/2001 | Morrison et al. |
| 6,294,550 B1 | | 9/2001 | Place et al. |
| 6,322,584 B2 | * | 11/2001 | Ingle et al. .................... 607/96 |
| 6,336,926 B1 | * | 1/2002 | Goble ........................... 606/34 |
| 6,425,877 B1 | * | 7/2002 | Edwards ....................... 604/21 |

\* cited by examiner

Primary Examiner—Linda C. M. Dvorak
Assistant Examiner—Ahmed M Farah
(74) Attorney, Agent, or Firm—Keaty Professional Law Corporation

(57) ABSTRACT

An apparatus and method for treating female stress-induced incontinence and other similar diseases associated with weakening of the pelvic floor muscles. A guiding catheter with temperature sensor(s) is positioned in patient's urethra. An inflatable balloon carried by a forward end of the catheter is inflated to sit in a neck of a bladder. Measuring indicia on the exterior of the catheter is indicative of a distance between the bladder neck and external meatus. A vagina probe member provided with a laser output in a forward portion thereof is then positioned in place such that the laser output is at about a level of the bladder neck, as facilitated by the guiding catheter. The laser output is operationally connected to a medical laser generating and monitoring device that delivers a laser beam to selected areas in the pelvic floor to cause denaturing and recoiling of the tissue collagen in the area surrounding the urethra. A cooling medium is circulated through the probe member to cool the immediately adjacent tissue. If temperature inside the urethra reaches a dangerous level, supply of the laser energy through the probe is terminated.

16 Claims, 3 Drawing Sheets

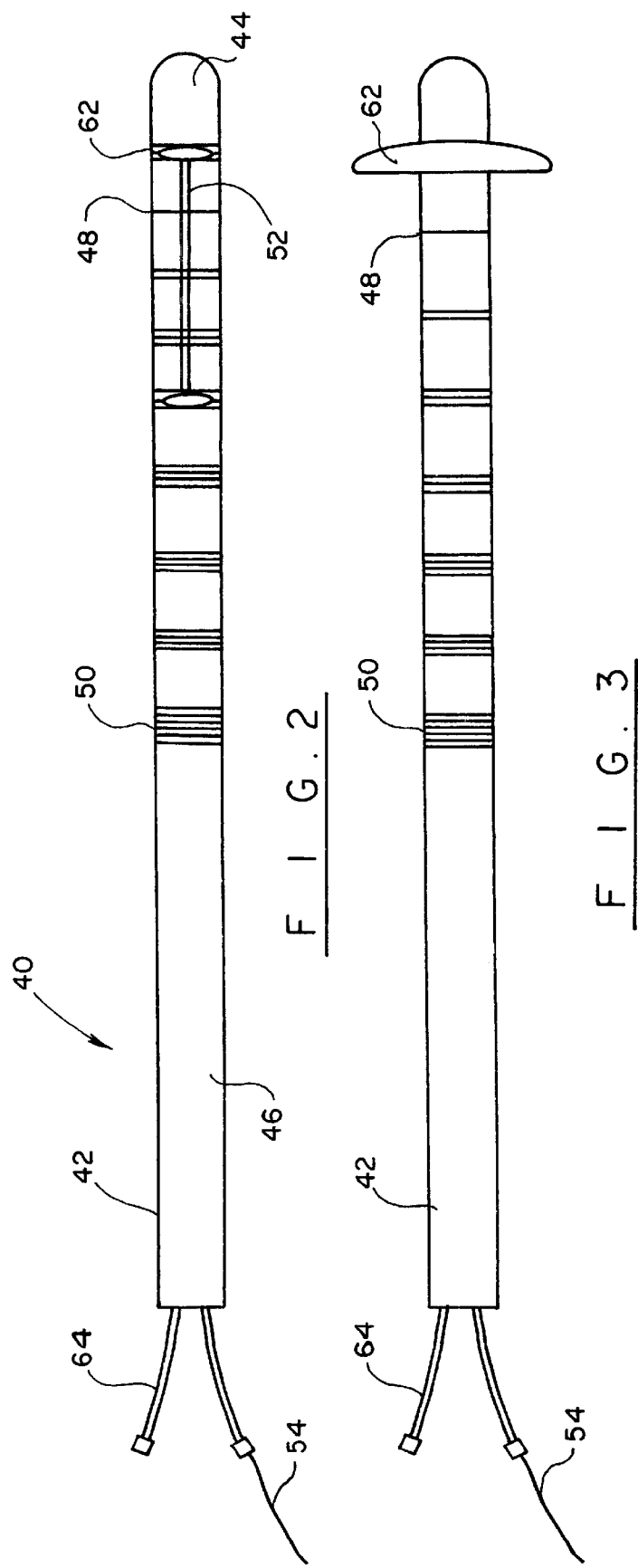

APPARATUS AND METHOD FOR TREATING URINARY STRESS INCONTINENCE

BACKGROUND OF THE INVENTION

The present invention relates to the field of surgery, and more particularly to an apparatus and method for surgical treatment of female urinary stress incontinence.

Stress-induced urinary incontinence (SUI) may be caused by a variety of activities, such as coughing, laughing, sneezing, exercising, lifting of heavy objects and other everyday activities. Sudden change of pressure in the intra-abdominal cavity causes the urethra to incompletely shut and leakage occurs. Such phenomenon usually takes place when there is an insufficient support of the urethra from the pelvic floor muscles and the structures within the muscles. A number of factors cause this effect: aging, vaginal deliveries of babies, changes in hormonal level, and others.

The present invention takes into consideration the fact that women suffering from the SUI show deficient levels of collagen in the matrix of the tissue that supports the urethra and the base of the bladder, the bladder neck. The supporting tissue resembles a trampoline that stretches underneath the bladder; when the support is weakened or sagging, the entire pelvic floor experiences changes that may lead to SUI, vaginal prolapse and other diseases.

Conventionally, SUI is treated with medications, injections or surgically. Most available medications have undesirable side effects, which limits their use. Some physicians recommend exercises to strengthen pelvic floor muscles. However, these exercises must be followed upon daily, otherwise their effectiveness is considerably reduced.

Some physicians use collagen injections into the urethra or bladder neck to cause coaptation of the urethra. Such injections are relatively expensive; the injection cycles must be repeated three or four times in a 12- or 18-month period and the success rate is about 70 percent at most. The injected collagen is metabolized, it migrates, or spreads into the surrounding tissue, and the desired bulking of the tissue almost disappears. Consequently, the injections must be repeated sometimes every six months, which further increases the cost of this type of treatment. Additionally, since the treatment usually involves injections of bovine collagen, the issue of mad cow disease takes another dimension.

Surgical procedures use a technique called the Pubo-Vaginal Sling. A strip of the patient's tissue, or a donor tissue, or a synthetic graft is surgically implanted around the urethra to strengthen the pelvic floor. Some of the strongest materials available, Pelvicol, is a homogenized collagen matrix made from pig's skin. The sling is implanted through the vagina, sometimes avoiding the need for an abdominal incision. As in many other surgical procedures, the skill of the operating physician is extremely important. If the sling is tensioned too tightly, it may interfere with the patient's urination, or the patients develop an overactive bladder—frequent involuntary contractions of the bladder. If the sling is too loose—the desired support has not been achieved.

A more recent procedure was suggested that involves application of radio frequency (RF) to the pelvic floor through the vagina. The theory behind this procedure is denaturing of collagen of the tissue surrounding the bladder by high frequency radio waves. It is expected that the denatured collagen will then recoil and tighten up the muscles. At this present time, this technology can only be achieved by first making a vaginal mucosal incision with mobilization of the vaginal mucosa off the underlying pelvic floor supporting matrix.

The present invention contemplates elimination of drawbacks associated with the prior art and provision of an apparatus and method for treating female stress urinary incontinence without having to incise the abdominal cavity or the vaginal mucosa.

SUMMARY OF THE INVENTION

It is, therefore, an object of the present invention to provide an apparatus for treating stress-induced urinary incontinence in women.

It is another object of the present invention to provide an apparatus for tightening pelvic floor muscles that support the bladder by denaturing collagen of the tissue and causing the tissue to recoil.

It is a further object of the present invention to provide a method of treating stress-induced urinary incontinence that does not require incision through the abdominal wall or vaginal mucosa.

It is still another object of the present invention to provide a method of treating stress-induced urinary incontinence that is minimally invasive.

These and other objects of the present invention are achieved through a provision of an apparatus for treating female stress-induced urinary incontinence and other similar diseases associated with weakening of the pelvic floor muscles. The apparatus of the present invention has a vagina probe member provided with a laser output in a forward portion thereof. The laser output is operationally connected to a medical laser generating and monitoring device that delivers a transmucosal laser beam to selected areas in the pelvic floor.

A temperature-conductive cover forms a portion of the probe member adjacent the laser output. A cooling medium is circulated behind the cover to cool the temperature of the tissue immediately surrounding the operation site (vaginal mucosa) where the laser beam is directed. The cooling medium, such as water, is supplied by a circulation pump operationally connected to the probe member through a suitable conduit attached to the handle of the probe member.

A guiding catheter with one or more temperature sensors is provided with an inflatable balloon adjacent to the forward end thereof. The guiding catheter is sized and shaped for positioning in urethra of the patient. When the catheter end reaches approximately the desired location, the balloon is inflated and a surgeon pulls slightly on the handle of the catheter to force the balloon to sit in the neck of the bladder. The catheter is provided with a measuring indicia on an exterior surface thereof to facilitate determination of the distance between the external meatus and the bladder neck.

The probe member is likewise provided with measuring indicia on the external surface thereof. Before the laser is activated, the surgeon notes the distance to the bladder neck to make sure that the laser output is at a level corresponding to the bladder neck.

The temperature sensors of the guiding catheter send a continuous signal to a temperature monitoring device and to the laser activation device. If the temperature inside the urethra exceeds the allowed pre-selected level, the monitoring device de-activates the laser and terminates the supply of energy to the probe member.

The tissue collagen of the selected areas affected by the laser energy denatures and recoils, causing tightening of the pelvic floor muscles, especially muscles surrounding the urethra. As a result, the stress-induced incontinence of the patient is minimized or even altogether eliminated.

BRIEF DESCRIPTION OF THE DRAWINGS

Reference will now be made to the drawings, wherein like parts are designated by like numerals, and wherein

FIG. 2 is a front view of the urethral catheter of the apparatus of the present invention with a balloon guide in a deflated condition.

FIG. 3 is a front view of the urethral catheter of the apparatus of the present invention with a balloon guide in an inflated condition.

DETAIL DESCRIPTION OF THE PREFERRED EMBODIMENT

Figure 1:
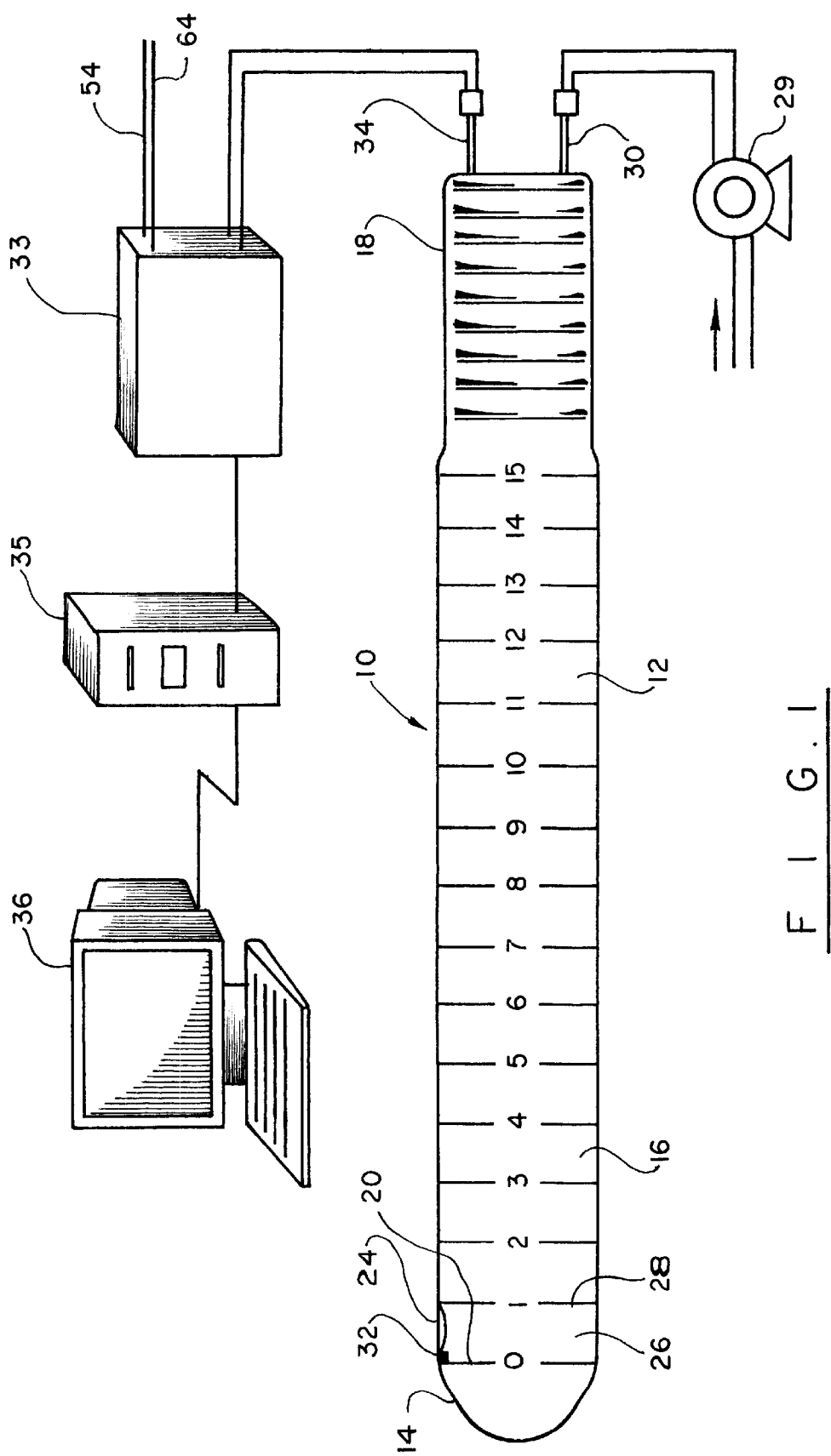
FIG. 1 is a front view of the laser probe of the apparatus in accordance with the present invention.

Turning now to the drawings in more detail, numeral 10 designates the laser probe of the apparatus of the present invention. As can be seen in FIG. 1, the laser probe 10 comprises an elongated generally cylindrical hollow body 12 with a rounded tip 14. The body 12 is divided into a laser portion 16 and a handle portion 18.

The exterior surface of the laser portion 16 is provided with a measuring indicia, dividing the length of the laser portion into cross segments representing the depth of positioning of the laser probe 10 in a vagina. The dividing lines may be 1 cm apart, starting from zero line 20, which is drawn adjacent the tip 14 and ending with a line 22 some 15 cm away from the line 20.

A window 24 is formed in a segment 26 between the line 20 and the immediately adjacent line 28. The window 24 is covered with a temperature-conductive crystal or plastic covering. Mounted in the body portion 12 behind the window 24 is a circulating line for circulating cooling fluid through the body 10. The circulating line exits the body 10 in a conduit 30, which is connected to a cooling medium circulating pump 29 shown schematically in FIG. 1.

The cooling fluid may be cooled sterile water or freon having a temperature sufficient to reduce the temperature of the operated site (vaginal mucosa) to a safe temperature of less than 40 degrees Centigrade. The temperature-conductive cover of the window 24 allows the circulating cooling medium to lower the temperature of the tissue immediately adjacent to the window 24.

Mounted adjacent to the window 24 is an output laser port 32 which allows laser energy to exit the body 10 during the surgery. The laser port 32 is connected by a cable 34 to a medical laser control device 33, which generates a laser beam and controls the energy delivered to the probe 10. The laser control device 33 generates a laser beam that is transmitted by a fiber optic cable to the laser output port 32. The control device 33 is provided with a calibration means to allow the surgeon to control the amount of energy delivered through the port 32. The laser control devices are conventional and do not form a part of the instant invention. The port 32 is relatively small to concentrate the area of operation and reduce a potential for damage to the mucous lining of the vagina.

The laser control device 33 is operationally connected to a computer 35 and to a video monitor 36, which allows the surgeon to monitor the procedure with a visual aid.

Turning now to FIGS. 2 and 3, the catheter guide 40 of the present invention is shown in more detail. As can be seen in the drawings, the catheter guide 40 comprises an elongated narrow body 42 sized and shaped to be safely inserted into the patient's urethra. The body 42 has a forward rounded tip 44 and a handle portion 46. The forwardmost portion of the catheter 40 carries a measuring indicia to assist in positioning of the probe 10, as will be explained in more detail hereinafter.

The first measuring line 48 is made a distance from the tip 44. The following measuring lines are made 1 cm apart, with the last line 50 being placed about 8–10 cm from the line 48. It is envisioned that when the probe 10 and the catheter 40 are in use, the zero lines 20 and 48 would appear at about the same depth in the patient's body.

One or more temperature sensors 52 are provided on the exterior of the body adjacent to the tip 44. The temperature sensors 52 are connected to cable 54, which extends through the interior of the body 42 and exits the body 42 for connection to a temperature-monitoring device 56. The temperature monitoring device 56 is, in turn, connected to the computer 35, which controls the laser probe 10. If the temperature inside the urethra exceeds the safe temperature of 45 degrees Celsius, the laser energy to the probe 10 is terminated.

Figure 4:
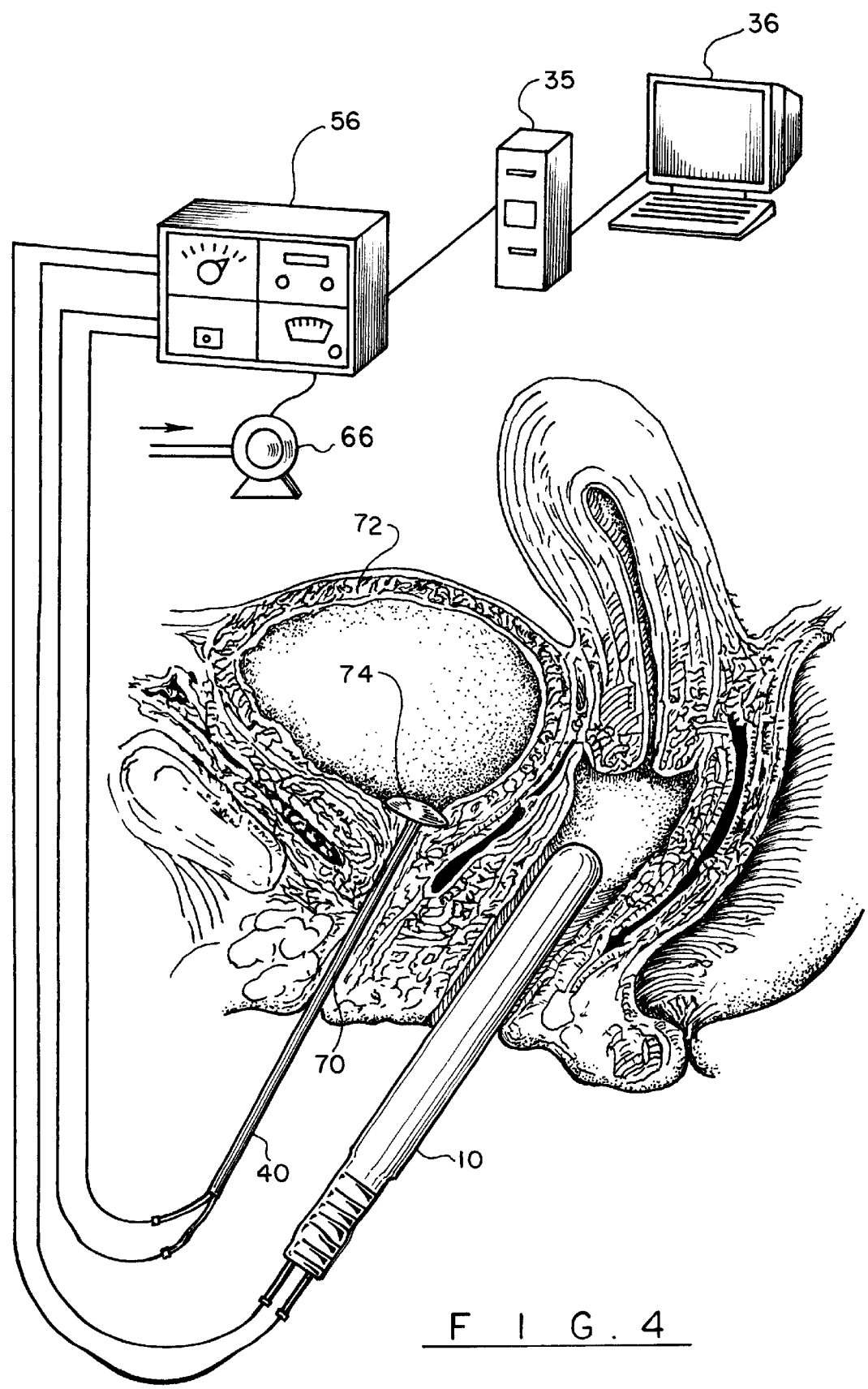
FIG. 4 is a schematic view showing position of the laser probe and the urethral catheter positioned adjacent the bladder being treated.

An inflatable balloon 62 is mounted on the body 42 between the tip 44 and the first measuring line 48. The balloon is connected to a conduit 64, which receives an inflating medium from a pump 66 (FIG. 4). The pump 66 supplies the fluid, for instance water, to the balloon 62 and inflates it after the catheter 40 has been positioned in the urethra and extends into the bladder.

It is preferred that the bladder of the patient is drained before the treatment is performed. Draining of the bladder may be also performed at the time when the catheter guide 40 is inserted into the urethra.

In operation, the surgeon first positions the catheter 40, maneuvering the catheter through the vagina into the urethra 70 so that the balloon 62 is inserted into the bladder 72. The balloon 62 is then inflated with water or other suitable substance. The surgeon pulls slightly on the body 42 such that the inflated balloon 62 sits in the neck 74 of the bladder 72. The surgeon may deviate the urethra laterally to limit the exposure of the urethra to the temperature created by a laser beam. The surgeon then notes the distance on the measuring lines of the catheter guide 40, indicative of the depth of insertion of the guide 40 from the external meatus to the bladder neck.

The temperature sensors 52 are activated to provide the surgeon with a readout of the actual temperature in the bladder 72. The surgeon then inserts the probe 10 through the vagina to a depth roughly corresponding to the neck 74 of the bladder 70, as indicated by the catheter 40 and the corresponding measuring lines on the probe 10. With the cooling system supplying cooling medium to the window 24 through the conduit 30, the surgeon activates the laser 32, sending laser energy to the tissue surrounding the probe 10.

The probe 10 with the side-firing laser 32 is rotated to treat the area about 2–3 cm square on both sides of the urethra. The temperature sensors 52 send a continuous signal to the computer 35. If the temperature inside the urethra reaches dangerous levels the computer 35 shuts off the laser energy to the laser probe 10, while the cooling system continues to run to bring the temperature inside the urethra back to a safe level. It is anticipated that the temperature in the range of 42–45 degrees Centigrade is safe for the bladder. Collagen denatures at about 65–75 degrees Centigrade. Consequently, the temperature created by the laser beam should not exceed 75 degrees Centigrade.

The laser beam burns the tissue in the target area, below the mucous lining, leaving a scar-like tissue behind. In time, the treated tissue tightens and pulls the pelvic floor muscles stronger. The collagen denaturing and recoiling phenomenon causes the muscles surrounding the urethra 70 to become stronger, building new tissue to eliminate sagging of the "trampoline" floor, that is of the muscular structure attached to the pelvic girdle.

The apparatus and method of the present invention may be used in a doctor's office, under a local anesthetic, thus minimizes the expense of the treatment and significantly lowers surgical and medical risks without having the patient stay in a hospital. The procedure described above does not require any incision, and the pain factor is minimized. However, it is envisioned that in some cases, patients would prefer to have the procedure done under monitored conscious sedation or regional anesthesia. In such a case, the surgeon may have the option of making a small incision in the anterior wall of the vagina, and the surgeon would use the hand-held probe 10 firing the laser beam to the tissue that he/she can actually see.

The apparatus and method of the present invention may be used for treating other diseases in addition to tightening the muscles under the urethra and straightening the pelvic floor adjacent to the neck of the bladder. It is envisioned that they may be used for treating pelvic floor prolapses, for treating the ladle wall of the vagina and pull up weakened ligaments, for treating anterior vaginal wall prolapse and others.

Many changes and modifications may be made in the apparatus and method of the present invention without departing from the spirit thereof. I, therefore, pray that my rights to the present invention be limited only by the scope of the appended claims.

I claim:

1. An apparatus for treating a pelvic floor of a human female patient, comprising:
    a vaginal hollow probe member having an elongated body with a forward portion and a handle portion, said forward portion being operationally connected with a means for delivering a laser energy to selected areas of pelvic floor muscles below mucous lining to prevent damage to vaginal mucosa;
    a means mounted in said body for circulating a cooling medium inside said body for cooling tissue surrounding said selected areas; and
    a transurethral catheter insertable to a depth corresponding to a neck of a patient's bladder, said catheter being provided with a temperature sensing means for terminating delivery of laser energy to said probe member when temperature of urethral tissue exceeds a pre-determined level.

2. The apparatus of claim 1, wherein said temperature sensing means monitors temperature inside the urethra when the means for delivering the laser energy are activated.

3. The apparatus of claim 2, wherein said guiding catheter comprises an elongated body carrying an inflatable balloon adjacent to a forward tip thereof, said balloon is adapted to sit in a neck of a bladder when inflated.

4. The apparatus of claim 1, wherein said probe member is sized and shaped for positioning in a vagina of a patient such that the forward portion extends to an area corresponding to a neck of a bladder.

5. The apparatus of claim 4, wherein said catheter and said forward portion are provided with a measuring indicia on an exterior surface thereof to facilitate positioning of the probe member at a substantially similar depth within patient's vagina and urethra, said depth corresponding to a neck of patient's bladder.

6. The apparatus of claim 1, wherein said means for operationally connecting the probe member with a means for delivering the laser energy comprises a laser generating and monitoring device having an output port formed in the forward portion of the probe member.

7. The apparatus of claim 1, further comprising a means operationally connected to said circulating means for delivering a cooling medium to said probe member, said delivering means comprising a pump for delivering a cooling medium to said forward portion and a heat-conductive cover mounted over a window formed in said forward portion for transmitting cooling temperature to the tissue surrounding the selected area, said delivering means being connected to a control means for continuous delivery of the cooling medium after de-activation of said means for delivering the laser energy and until a pre-determined temperature in the urethra has been detected.

8. The apparatus of claim 1, further comprising a control and video monitoring means for providing a continuous data on the temperature inside the urethra and the laser energy being delivered to the probe member.

9. An apparatus for treating female stress induced incontinence, comprising:
    a hollow probe member having a body with a forward portion and a handle portion, said forward portion adapted for positioning in vagina of a patient without damaging vaginal mucosa, said probe member being operationally connected with a means for delivering a laser energy to selected areas of pelvic floor muscles and to a means for cooling tissue surrounding said selected areas;
    a guiding catheter sized and shaped for positioning in urethra of a patient, said guiding catheter being provided with a temperature sensing means for monitoring temperature inside the urethra when the means for delivering the laser energy are activated, said guiding means being provided with a measuring indicia on an exterior surface thereof to measure the distance to the neck of the bladder from an entry point of said guiding catheter into external meatus to facilitate correct positioning of the probe member; and
    a control and video means for monitoring delivery of laser energy to selected muscular tissue and for terminating delivery of laser energy when temperature detected by said temperature sensing means exceeds a pre-determined level, said control means continuing operation of the cooling means until temperature of the urethra decreases to a pre-determined level.

10. The apparatus of claim 9, wherein said forward portion is provided with a measuring indicia on an exterior surface thereof to facilitate positioning of the forward portion of the probe member at a level corresponding to a neck of a bladder.

11. The apparatus of claim 9, wherein said means for operationally connecting the probe member with a means for delivering the laser energy comprises a laser generating and monitoring device having an output port formed in the forward portion of the probe member.

12. The apparatus of claim 9, wherein said means for operationally connecting the probe member to a cooling means comprises a pump for delivering a cooling medium to said forward portion and a heat-conductive cover mounted over a window formed in said forward portion for cooling the tissue surrounding the selected area.

13. The apparatus of claim 9, wherein said guiding catheter comprises an elongated body carrying an inflatable balloon adjacent to a forward tip thereof, said balloon is adapted to sit in a neck of a bladder when inflated and facilitate determination of a distance from the external meatus to the neck of the bladder.

14. A method of treating female stress-induced incontinence, comprising the steps of:
  providing a vaginal probe member having a laser output port in a forward portion thereof;
  providing measuring indicia on the forward portion of the probe member;
  providing a guiding catheter sized and shaped for positioning in urethra of a patient;
  providing measuring indicia in an exterior surface of the guiding catheter and an expandable balloon adjacent a forward end of the guiding catheter;
  positioning said guiding catheter in urethra of the patient such that a forward end of the guiding catheter extends to a neck of a bladder of the patient;
  inflating the balloon and seating the balloon against the neck of the bladder;
  noting a distance between the forward end of the guiding catheter and external meatus;
  with reference to measuring indicia observed on the guiding catheter, positioning the probe member in such manner that a forward portion of the probe member extends to a level corresponding to the neck of the bladder;
  providing a temperature-conductive window in the forward portion of the probe member adjacent the laser output;
  providing a means inside said probe member for delivering cooling medium to a location behind said temperature-conductive window;
  activating delivery of a cooling medium to the probe member;
  delivering laser energy to selected areas surrounding urethra at the level of the bladder neck to cause denaturing of tissue collagen and recoiling of the tissue below mucous lining of the vagina without causing damage to vaginal mucosa, while continuously monitoring temperature inside the urethra; and
  de-activating delivery of the laser energy when temperature inside the urethra exceeds a pre-determined level, while continuing circulation of the cooling medium until temperature of the selected area decreases to a pre-determined level.

15. The method of claim 14, further comprising the step of providing said guiding catheter with a temperature-sensing means operationally connected to a temperature monitoring device and to a laser energy generating means.

16. The method of claim 14, wherein said laser output port of the probe member is operationally connected to a laser generating and monitoring device.

* * * * *